United States Patent
Chan et al.

[11] Patent Number: 6,008,241
[45] Date of Patent: * Dec. 28, 1999

[54] GREEN PORPHYRINS AS IMMUNOMODULATORS

[75] Inventors: Agnes H. Chan, Fort Moody; David W. C. Hunt, White Rock; Julia G. Levy, Vancouver; Modestus O. K. Obochi, Vancouver; Anna M. Richter, Vancouver; Guillermo O. Simkin, North Vancouver, all of Canada

[73] Assignee: QLT PhotoTherapeutics, Inc., Vancouver, Canada

[*] Notice: This patent is subject to a terminal disclaimer.

[21] Appl. No.: 08/856,921

[22] Filed: May 16, 1997

Related U.S. Application Data

[63] Continuation-in-part of application No. 08/374,158, Jan. 17, 1995, Pat. No. 5,789,433.

[51] Int. Cl.$^6$ .................................................. A61K 31/40
[52] U.S. Cl. ........................................................... 514/410
[58] Field of Search ............................................. 514/410

[56] References Cited

U.S. PATENT DOCUMENTS

| | | |
|---|---|---|
| 4,883,790 | 11/1989 | Levy et al. . |
| 4,920,143 | 4/1990 | Levy et al. . |
| 5,095,030 | 3/1992 | Levy et al. . |
| 5,171,749 | 12/1992 | Levy et al. . |
| 5,283,255 | 2/1994 | Levy et al. . |
| 5,422,362 | 6/1995 | Vincent et al. . |
| 5,484,804 | 1/1996 | Achard et al. . |

FOREIGN PATENT DOCUMENTS

| | | |
|---|---|---|
| 0 284 409 | 9/1988 | European Pat. Off. . |
| WO 91/12801 | 9/1991 | WIPO . |
| WO 95/03797 | 2/1995 | WIPO . |
| WO 96/21466 | 7/1996 | WIPO . |
| WO 96/22090 | 7/1996 | WIPO . |
| WO 97/09043 | 3/1997 | WIPO . |

OTHER PUBLICATIONS

Mathews–Roth, M.M. "Porphyrin photosensitization and carotenoid protection in mice; in vitro and in vivo studies" *Chemical Abstracts* 101(15):329–330(1984), Abst. No. 125996.

Richter, A.M. et al. "Photodynamic treatment with BPD–MA (verteporfin) activated with light within different spectral ranges" *Proc. SPIE–Int. Soc. Opt. Eng.* 3191:15–24 (1997).

Simkin, G. et al. "Effect of photodynamic therapy using benzoporphyrin derivative on the cutaneous immune response" *Proc. SPIE–Int. Soc. Opt. Eng* 2392:23–33 (1995).

Simkin, G.O. et al. "Inhibition of contact hypersensitvity with different analogs of benzophorphyrin derivative" *Immunopharmacology* 37:221–230 (1997).

Taylor, P.W. "Liposomal Delivery of Photosensitizers" *J. Liposome Research* 6(1):185 (1996).

Bae, J. et al., *J. Invest Dermatol.* (1996) 106:950.

Elmets, C. A. et al., *Cancer Res.* (1986) 46:1608–1611.

Gruner, S. et al., *Scand. Journal Immunol.* (1985) 21:267–273.

Gruner, S. et al., *Tissue Antigens* (1986) 27:147–154.

Hunt, D.W.C. et al., *Immunopharmacology* (1993) 26(3):203–212.

Hunt, D.W.C. et al., *Proceedings of SPIE* (1997) 2972:110–121; Proceedings of Association Internationale de Photobiologie, Vienna, Austria 1996.

Leong, S. et al., *Photochem. Photobiol.* (1996) 64:751–757.

Levy, J.G., *Seminars in Oncology* (1994) (Suppl. 21(6)) 15:4–10.

Levy, J.G., *Stem Cells* (1995) 13(4):336–343.

Simkin, G. et al., Proceedings of Optical Methods for Tumor Treatment and Detection: Methods and Techniques in Photodynamic Therapy IV—SPIE The International Society for Optical Engineering, San Jose, CA, 4–5 Feb. 1995, 2392:23–33.

*Primary Examiner*—John M. Cooney, Jr.
*Attorney, Agent, or Firm*—Morrison & Foerster LLP

[57] ABSTRACT

Green porphyrins act as antigen-specific immunomodulators in the active phase of an immune response to a particular antigen. This effect occurs at ambient light levels.

15 Claims, 6 Drawing Sheets and

Overlap BPD-RGD from Group A

Overlap BPD-RGD from Group B

Overlap BPD-RGD from Group C

GREEN PORPHYRINS AS IMMUNOMODULATORS

CROSS REFERENCE TO RELATED APPLICATION

This application a continuation-in-part of U.S. Ser. No. 08/374,158, filed Jan. 17, 1995, now U.S. Pat. No. 5,789,433 the entire contents of which are incorporated herein by reference. Priority of the prior-filed application is claimed under 35 U.S.C. § 120.

TECHNICAL FIELD

The invention is in the field of modulating immune responses by administering green porphyrins at levels of light that approximate ambient conditions. Antigen-specific immune responses are modulated when the green porphyrins are administered during the course of the response to a specific antigen.

BACKGROUND ART

A group of compounds useful in photodynamic therapy, collectively designated green porphyrins, is disclosed in a series of patents including U.S. Pat. Nos. 5,283,255; 4,883,790; 4,920,143; 5,095,030; and 5,171,749, the disclosures of which are incorporated herein by reference. These green porphyrins are prepared using a Diels-Alder reaction with protoporphyrin IX and optional rearrangement or reduction of the resulting product. A particularly preferred form of these green porphyrins, as outlined in the above-referenced patents, is designated a benzoporphyrin derivative in the monoacid form, or "BPD-MA". This drug is currently in clinical trials with respect to photodynamic treatment of various tumors and other conditions.

Photodynamic therapy rests on the assumption that the photoactive compounds administered, in this case the green porphyrins, are without physiological effect in the absence of light. However, when irradiated, the excited forms of the compounds exert local toxic effects. Therefore, for the treatment of tumors, for example, advantage has been taken of the tendency of these photoactive compounds to be retained in tumor tissue after clearance from normal tissue has been effected. It has also been found that local irradiation to areas of neovasculature is effective even before the compounds have been cleared from normal tissue. This "early treatment" is described in copending application Ser. No. 08/391,414, now U.S. Pat. No. 5,705,518 and incorporated herein by reference. However, the timing of treatment in terms of pharmacokinetics has generally been discussed in terms of tumor treatment, and is generally not applicable to use for immunomodulation.

In addition, it is known to apply light to affect cells in the blood stream or elsewhere transcutaneously. U.S. Pat. No. 5,484,804, describes this form of light application which, in regard to tissue targets, can be done after homing of the drug to the target tissue or can be done prior to the opportunity of the drug to home—i.e., before the drug clears normal tissue.

The potential applicability of photodynamic treatment per se to modulating the immune response has been known for some time. For example, Gruner, S. et al. *Scand J Immunol* (1985) 21:267–273, studied the influence of PDT using hematoporphyrin derivative on murine skin graft survival, epidermal Langerhans cells, and stimulation of the allogeneic mixed leukocyte reaction. As a result of their studies, the authors concluded that hematoporphyrin derivative and visible light interfere with the function of antigen-presenting cells. An additional paper by Gruner, S. et al. *Tissue Antigens* (1986) 27:147–154, found a similar result when psoralen was used as the photosensitizing agent. A paper by Elmets, C. A. et al. *Cancer Res* (1986) 46:1608–1611, reports studies using hematoporphyrin derivative in PDT protocols where such PDT protocols were shown to inhibit the delayed-type hypersensitivity or contact hypersensitivity (CHS) reaction in mice using dinitrofluorobenzene (DNFB) as the sensitizing antigen. An immunomodulating effect was found. The authors further note that "mice treated with HPD alone and sensitized to DNFB on the same day "developed a slight but statistically significant ($p<0.02$) suppression of contact sensitivity." This was said to be considerably less than that obtained using the PDT regimen and the authors hypothesized that "Although HPD alone may be directly immunosuppressive, we cannot exclude the possibility that these might have been inadvertently exposed to small amounts of ambient light that was sufficient to produce mild immunosuppression."

The present applicants, in a report by Simkin, G. et al. *Proceedings of "Optical Methods for Tumor Treatment and Detection: Methods and Techniques in Photodynamic Therapy IV" SPIE-The International Society for Optical Engineering*, San Jose, Calif., Feb. 4–5, 1995, studied the effect of PDT in the DNFB-based contact hypersensitivity (CHS) model as well as on acceptance of allogeneic skin grafts in mice. The authors found that transdermal PDT effectively inhibited the CHS response against DNFB and was helpful in extending the survival time of skin allografts. Indeed, copending application Ser. No. 08/371,707 which is now abandoned and Ser. No. 08/759,318 which is now U.S. Pat. No. 5,882,328 both incorporated herein by reference, describe the use of photodynamic therapy, including the use of green porphyrins in these regimes to reduce the rejection of allografts. In addition, U.S. Ser. No. 07/889,707, which is now U.S. Pat. No. 5,776,966 and incorporated herein by reference describes the ability of photodynamic therapy using green porphyrins to selectively reduce activated leukocyte cell populations.

U.S. Ser. No. 08/309,509 which is now U.S. Pat. No. 5,807,881 describes the use of photodynamic therapy in treating multiple sclerosis and rheumatoid arthritis as exemplary of autoimmune diseases. In addition, U.S. Pat. No. 5,368,841 describes direct PDT on synovial joints for the same purpose.

The present applicants have also disclosed the effect of PDT using BPD-MA on dendritic cells, which are potent antigen-presenting cells (APC). Treating purified dendritic cells with BPD-MA in vitro in the dark and then exposing these cells to 5 $J/cm^2$ of 690 nm light resulted in a decrease in expression of MHC Class I and Class II antigens, in expression of ICAM-1 (CD54) and in expression of CD80 and CD86. Expression of leukocyte function associated-1 (LFA-1, CD11a) and the DEC-205 receptor were increased after this treatment while CD45, CD11b (MAC1) and CD18 (integrin β2 chain) were not affected. In addition, dendritic cells treated in this manner were poor stimulators of the allogeneic T cells in a mixed lymphocyte reaction. In the absence of light, there was no effect on the immunostimulatory properties. These results were reported at symposia in Vienna 1996 and San Jose 1997: Hunt, D. W. C. et al., *Proceedings of SPIE* (1997) 2972:110–121; *Proceedings of 'Association Internationale de Photobiologie'* Vienna, Austria 1996.

Regulating light levels in PDT was studied in connection with the porphyrin precursor ALA by Bae, J. et al. as reported in *J Invest Dermatol* (1996) 106:950. It was found that low levels of light were effective in enhancing phototoxicity of this precursor compound.

In addition, U.S. Pat. No. 5,422,362, shows the ability of green porphyrins in the absence of light (as opposed to photodynamic treatment) to inhibit restenosis caused by trauma to the blood vessels. The disclosure of this patent is also incorporated herein by reference.

The present applicants have also shown that transcutaneous photodynamic therapy alters the development of murine experimental autoimmune encephalitis (EAE). Leong, S. et al. *Photochem Photobiol* (1996) 64:751–757.

It has now been found that the green porphyrins have immunomodulatory activity at light levels that correspond to those of ambient light, independent of the more intense light administered either directly to the tissue or transcutaneously. The present invention takes advantage of this property, hitherto unexpected, of the green porphyrins.

DISCLOSURE OF THE INVENTION

The invention takes advantage of the ability of green porphyrins, without direct or transcutaneously administered irradiation, to influence an immune response generated against a known or as yet unidentified specific antigen. The resulting immunomodulation is antigen-specific in the sense that the effects are substantially confined to the condition to be treated, so that the subject can be protected against unwanted responses with respect to autoantigens, allergens and the like without the disadvantage of being immunocompromised generally.

Thus, in one aspect, the invention is directed to a method to modulate an antigen-specific immune response, which method comprises administering to a subject who is experiencing an unwanted activated immune response to an antigen, an amount of green porphyrin effective to modulate said immune response to the antigen, in the presence of light at levels which approximate ambient, wherein said administering is during the active phase of the immune response to the specific antigen per se.

It will be recognized that light that approximates ambient is well below the total light energy that would be utilized in standard photodynamic therapy. The levels characteristic of PDT can be ascertained empirically for any given subject by administering a photoactive agent and then testing a small portion of the skin of the subject at various levels of light energy. The level at which the subject shows erythema or redness of the skin is taken as the minimum level for PDT. An ambient approximate dosage will be approximately only one-quarter or one-sixth of this level.

In related aspects, the invention is directed to applying the immunomodulating methods of the invention to specific conditions where an unwanted immune response is associated with a particular antigen, identified or unidentified. These conditions include allograft transplantation, autoimmune diseases such as rheumatoid arthritis, multiple sclerosis, lupus erythematosus and the like as well as allergic reactions.

In other aspects, the invention includes formulations of green porphyrins useful in the method of the invention.

MODES OF CARRYING OUT THE INVENTION

Figure 1:
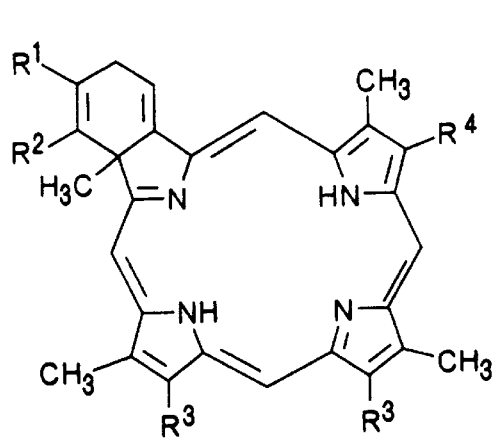
FIG. 1 shows representative structures for the green porphyrins useful in the methods of the invention.

There are numerous instances in which an immune response to a particular antigen is undesirable. Prominent among these situations are allergic responses, autoimmune responses, and immune rejections of organ transplants, skin grafts and the like. The green porphyrins of the invention are effective when administered in the active phase of eliciting an immune response, and are thus effective when administered in the time period following exposure to the antigen, or if the immune response in its active form is continuous, during this continuous phase. The subjects that are candidates for the modulation of immune response according to the method of the invention include those subjects with developed immune systems, typically any vertebrate subject. Thus, the methods of the invention are designed for the treatment of human patients as well as other mammalian and avian vertebrates, for example.

The green porphyrins exert their effects in the presence of radiation of appropriate wavelengths and in an intensity and total energy that corresponds to ambient light. Thus no deliberate radiation of the target is employed and normal light conditions, either daylight or artificial or both are sufficient. As described in the Background section above, green porphyrins have been used extensively in photodynamic therapy protocols. In these protocols, a group of cells or a tissue modified to contain substantial amounts of the green porphyrin is deliberately irradiated with light including wavelengths absorbed by the green porphyrin compounds. The absorption of these wavelengths by the green porphyrins results in excitation of the molecules in such a way that surrounding materials are damaged. It is assumed that singlet oxygen is generated by transfer of energy from the excited compounds to molecular oxygen which accounts for the toxicity. Interaction of singlet oxygen with oxidizable biological molecules is considered responsible for this effect. The photoactive agent itself, is presumed to be nontoxic.

In the methods of the present invention, direct or transcutaneous irradiation with light to effect excitation is not included in the protocol. Ambient light levels are sufficient. Blockage of all light from the subject being treated, however, obviates the effect. Thus, while the use of PDT to effect immunomodulation has been known for some time, the ability of the green porphyrins to exhibit this activity at low dosage levels both of photoactive compound and of light is surprising.

As used herein, the phrase "under conditions of ambient light" means light as typically found under ordinary working conditions. The light may be supplied by sunlight or artificial light. The artificial light may originate from incandescent, fluorescent, or halogen lamps and can include other sources such as LEDs. No special arrangement to supply light need be made, and the expense of dedicated or complex light sources is avoided.

It is understood that ambient light may vary with location and the habits of the practitioner. However, a broad range of light intensities is acceptable as is a broad range of total light dosage. It appears that a useful minimum dosage is of the order of 0.2 $J/cm^2$, preferably 0.5 $J/cm^2$, more preferably 1 $J/cm^2$. Of course, higher energies can be supplied; typical total energies employed in PDT using Photofrin®, for example, are typically 200 $J/cm^2$ or higher. Thus, low-dose PDT would employ energies of 10 $J/cm^2$ or less.

As described infra, the minimum total energy associated with PDT for the green porphyrin can be determined empirically for any subject and the radiation employed will be only a fraction of this total energy.

The intensity of the light used to supply the total light level appears to be inconsequential within a reasonable range. However, the intensities are typically lower than those employed in conventional PDT, where it is believed that intensities as low as 5 mW/cm² for extended time periods can be used (see, for example, U.S. Pat. No. 5,145, 863). Nevertheless, in conventional PDT, intensities in the range of 160 mW/cm² are employed, and intensities as high as 1 W/cm² have been used. As shown in the examples herein, the light intensities employed in the present invention are typically in the range of 100 $\mu$W/cm² and intensities of less than 5 mW/cm², preferably less than 1 mW/cm², more preferably less than 500 $\mu$W/cm², are generally used. A preferred range is 100–400 $\mu$W/cm² for 5–6 hours. The light is applied generally during the course of administration of the green porphyrin and can be continuous over substantial time periods. There is no need to wait, however, for any "homing" of the green porphyrin, although an intervening period of darkness is permissible.

As will be clear from the foregoing, the levels of ambient light supplied are of sufficiently low intensity that the destruction of living cells that occurs in ordinary photodynamic therapy is avoided. The intensities and total energies supplied are such that the immune function is modulated, but the cells of the subject remain viable. As described below, a useful maximum light level can be determined empirically by isolating a portion of the skin and treating with varying total energies of light after the drug has been administered to determine the threshold level of the true photodynamic effect. Light intensities and energies below this level are maintained.

Green Porphyrins

The nature of the green porphyrins is described in the patents referenced in the Background section hereinabove. Briefly, these are derivatives of protoporphyrin IX that are obtainable using a Diels-Alder reaction with a substituted acetylene, optionally followed by rearrangement and/or reduction. Typical formulas for the compounds thus obtained are shown in FIG. 1. Preferred embodiments of the formulas shown in FIG. 1 are those wherein the ring system has the formulas shown in FIGS. 1–3 or 1–4; and/or wherein each of $R^1$ and $R^2$ is independently selected from the group consisting of carbalkoxyl (2–6C), alkyl (1–6C), arylsulfonyl (6–10C), cyano; and —CONR⁵CO— wherein $R^5$ is aryl (6–10C) or alkyl (1–6C); each $R^3$ is independently carboxyl, carboxyalkyl (2–6C) or a salt, amide, ester or acylhydrazone thereof or is alkyl (1–6C); $R^4$ is CH=CH₂ or —CH(OR⁴') CH₃ wherein $R^{4'}$ is H, or alkyl (1–6C) optionally substituted with a heteroatom substituent. Of course, mixtures can be used.

Particularly preferred are those compounds of FIGS. 1–3 and 1–4 wherein each of $R^1$ and $R^2$ is independently carbalkoxyl (2–6C); one $R^3$ is carboxyalkyl (2–6C) and the other $R^3$ is the ester of a carboxyalkyl (2–6C) substituent; and $R^4$ is CH=CH₂ or —CH(OH)CH₃.

Especially preferred are the compounds shown as FIGS. 1–3 and 1–4 wherein $R^1$ and $R^2$ are methoxycarbonyl; both $R^3$ are —CH₂CH₂COOH or wherein one $R^3$ is —CH₂CH₂COOCH₃ and the other $R^3$ is CH₂CH₂COOH; and $R^4$ is CH=CH₂. These compounds are referred to as BPD-DA and BPD-MA, with respect to FIGS. 1–3 and as BPD-DB and BPD-MB for FIGS. 1–4. These are acronyms for benzohydroporphyrin derivative diacid or monoacid wherein the Diels-Alder addition occurs on ring A or ring B respectively. Preferred among these are BPD-MA and BPD-MB, especially BPD-MA.

In addition, preferred compounds include compounds shown as FIGS. 1–3 and 1–4 wherein $R^1$ is carboxyl, $R^2$ is methylcarbonyl, both $R^3$ are —CH₂CH₂COOH and $R^4$ is —CH=CH₂. These forms, designated the "triacid" forms, are described in copending U.S. application Ser. No. 08/852, 326 filed May 7, 1997. Also described in copending U.S. application Ser. No. 08/852,494 filed May 7, 1997 is an additional preferred form designated EA6 which is of the formula 1–4 where $R^1$ and $R^2$ are methylcarbonyl, both $R^3$ are —CH₂CH₂COOCH₂CH₂OH, and $R^4$ is vinyl. Additional members of the class of photosensitizers designated green porphyrins herein are disclosed in these copending applications which are incorporated herein by reference.

Nature of the Conditions Treated

The green porphyrins, when administered to a vertebrate subject during the course of an activated immune response to a particular antigen or group of antigens, modulate the response to the specific antigen when the subject is exposed to ambient light without resulting in systemic or general immunosuppression. The timing of administration is facilitated if the subject is naive with respect to the immunogen/ antigen administered. Unwanted immune responses to deliberately administered antigens are found, for example, in transplantation protocols using allografts, such as skin transplants or organ transplants, individual cellular transplants, such as those used in insulin replacement for diabetes, and any other surgical procedure or procedure involving injection wherein foreign cells or tissues are deliberately introduced into the subject. Other instances where an unwanted immune response may occur to a deliberately administered compound include those wherein proteins of species xenogeneic to those of the subject are used. A typical example is the administration of monoclonal antibodies in the treatment of tumors. In many cases, although attempts at humanizing antibodies have been made, monoclonal antibodies derived from mice are used in human therapy. An undesired immune response to such antibodies can be modulated by the methods of the invention. In these instances, a primary immune response is activated and the administration of green porphyrins contemporaneously with or immediately following the administration of the antigen provides the desired effect.

Another instance wherein an immune response occurs to a foreign antigen, is illustrated by allergic reactions. While these responses are generally secondary immune responses, administration of the green porphyrins of the invention simultaneously with this secondary exposure, or in a time period proximal thereafter, is also effective.

In both of the foregoing cases, the green porphyrin will be administered at the same time that the antigen or allergen is administered or within the time period required for the active response to the antigen. In general, this time period is within 72 hours, preferably within 48 hours, and more preferably within 24 hours of the administration of antigen. Administration of the green porphyrin at the same time, or after antigen is given to the subject as preferred.

In general, the green porphyrin may be administered either before or after or along with the administration of the antigen within this general time period. The ambient light should be present for suitable time periods subsequent to the administration of the green porphyrin, and preferably subsequent to administration of the antigen. Thus, typical protocols might include, designating the time of antigen administration at time zero:

green porphyrin at −48 hours; ambient light present from −24 hours−+24 hours for at least two 12-hour periods;

green porphyrin at +24 hours; ambient radiation for 5 hours beginning at 24 hours and ending at 29 hours;

green porphyrin administration at time zero; ambient radiation from +10 hours−+22 hours;

green porphyrin administration at −12 hours; ambient radiation from zero hours−+6 hours.

For some indications, there is a clear preference for administering the green porphyrin subsequent to antigen administration. Thus, administration within the above-stated periods but at the time of or subsequent to administration of antigen is preferred.

It will be recalled that in this context the "antigen" will be, for example, donor transplantation tissue or a foreign protein, such as a murine monoclonal antibody.

In addition, the donor tissue itself can be pretreated with the green porphyrin and low light doses prior to transplantation. Typical patients would be treated with a low dose of green porphyrins followed by prolonged exposures to very low light between 1 hour and 72 hours after administration of the drug.

If the condition for treatment is an autoimmune response, the autoantigen or antigens, whether now known or still to be identified, is presumably continuously present, and administration of the green porphyrins and ambient radiation would occur at any time that is convenient for the subject. Particularly preferred times, however, would be during the period where symptoms are evidenced.

The subjects for whom the methods of the invention are appropriate are generally vertebrate subjects, preferably mammalian subjects. Particularly preferred subjects are domesticated animals and avian subjects, as well as human subjects. The appropriate protocols, dosage, and formulation will depend, of course, on the nature of the subject.

Administration of the Antigen

The administration of the antigen simultaneously with or proximally before the administration of the green porphyrin will vary depending on the nature of the antigen. For deliberately administered antigens, such as drugs, monoclonal antibodies or other foreign proteins which are used for therapeutic or diagnostic purposes, the dosage level and form of administration will be controlled by the purpose for which the antigen is administered generally. The antigen is typically already available in a suitably formulated pharmaceutical composition and the dosage levels and expected routes of administration are already known.

With respect to allografts, it is generally believed that the cells that define tissues or organs from members of the same species as the intended recipient, including vascularized organs such as the heart, kidney, liver, lungs, etc. and endocrine glands such as pituitary, thyroid, adrenal, parathyroid and pancreas and skin grafts, while potentially immunogenic, may not contain the necessary major histocompatibility complex (MHC) antigens to trigger immune-based rejection of the transplant. Rather, these antigens are believed to be expressed by passenger cells such as leukocytes that are present in the transplanted cells.

Thus, the administration of the green porphyrin can either be performed at the time of, or approximately after, the transplant itself carrying the disparate MHC-bearing cells, or the subject may be protected in advance by administering the relevant histocompatibility antigens separately, either as proteins per se, or included on the surfaces of cells bearing them. The green porphyrin is then administered at a time proximal to the preadministration of the cells or histocompatibility antigens. For example, a major determinant of histocompatibility in humans is designated HLA-DR in the group of MHC Class II antigens. These have been subclassified, and if the donor has been typed, the subtype of DR antigen can be administered along with proximal administration of the green porphyrin prior to the transplant per se.

If the antigen is an allergen, the allergen can be administered directly by injection or orally along with the green porphyrin or immediately prior to administration of the green porphyrin. Alternatively, the administration may mimic natural exposure by placing the subject in proximity to, for example, plants which contain pollen known to elicit an allergic response in the subject. When the subject is placed in this environment, green porphyrin is administered simultaneously or very soon thereafter.

If the antigen is an autoantigen, such as believed responsible for a number of conditions including rheumatoid arthritis, multiple sclerosis, lupus erythematosus, certain types of diabetes, or inflammatory reactions generally caused by an autoantigen, the administration of the antigen cannot be separately controlled. The efficacy of the method of the invention depends on the continuing active immune response to the autoantigen which is supplied internally. In this case, the green porphyrin is administered to the subject afflicted with the autoimmune disease, preferably during episodes when the immune response is most evident.

An additional condition believed to be related to an autoimmune response is psoriasis. The method of the invention is thus suitable for treatment of this condition.

Formulation and Administration

The green porphyrins of the invention may be formulated and administered in a manner convenient generally for small-molecule drugs as is known in the art, for example, as set forth in *Remington's Pharmaceutical Sciences*, Mack Publishing Company, Easton, Pa., Latest Edition. The composition will contain a quantity of the green porphyrin effective to provide immunomodulation. The dosage level will vary depending on the mode of administration, formulation, condition to be treated, and the nature of the subject; however, in general, the amount of green porphyrin for systemic administration is of the order of 10 $\mu$g/kg to 100 mg/kg, preferably 100 $\mu$g/kg-10 mg/kg, and most preferably about 1 mg/kg in mice and about 0.2 mg/kg in humans. Various metabolic factors influence the resultant plasma levels obtained by systemic administration and plasma level determines concentration in target cells. Thus, species differences are expected. If administration is topical, suitable concentrations in the composition ranging from about 5% to about 95% of the composition, preferably about 10%–50% of the composition are employed.

Routes of systemic administration can be by injection, including intravenous, intramuscular, intraperitoneal and the like; oral, transmucosal or transdermal using appropriate excipients, and the like. Localized administration can be achieved also by transdermal or transmucosal means using suppositories or skin patches or the green porphyrins may be applied topically in the form of gels or salves.

When systemic administration is employed, liposomal compositions are particularly preferred. Liposomes can be prepared using standard methods; they typically are prepared from negatively charged phospholipids such as phosphatidyl glycerol, phosphatidyl serine or phosphatidyl inositol as well as lipids per se and various stabilizing agents. The liposomes may be multilamellar or unilamellar and are in a range of sizes. The concentration of green porphyrin in the liposomal composition is typically on the order of 1–20%.

The application of ambient light generally needs little attention. Assuming that normal room illumination and daylight or artificial light are present and can reach the skin of the subject as would normally be the case during treatment with the green porphyrin and at normal waking times thereafter, this is sufficient to assure the immunomodulatory effect. Accordingly, it is generally not necessary to devise a specific protocol to supply the ambient light. If it is desirable to control ambient light levels, this can be accomplished using ordinary optimization protocols. It is, of course, possible simply to advise the subject to stay consistently before a relatively weak light source, such as less than 5 mW/cm$^2$, much lower than an intensity required for PDT, for a limited time period.

It is permissible to use low levels of deliberately administered light as well. The levels, however, should be only about one-fourth, preferably only about one-sixth of the minimal levels are needed to produce a true photodynamic effect. The minimal total energy for PDT can easily be ascertained by irradiating a limited portion of the subject's skin with varying total energies of light after the drug as been administered. The level of energy at which erythema develops is the threshold of the true photodynamic effect. The levels used to treat the subject in the affected areas or over the whole body are then calibrated as fractions of this amount.

The effective activation of the drug occurs at total energies of less than 10 J/cm², typically less than 5 J/cm², more preferably 1 J/cm² or less on the order of 0.2–0.5 J/cm². This total dosage is typically delivered over a relatively short time period, less than 3 days, preferably less than 2 days and more preferably less than 1 day. Shorter times can also be employed.

The following examples are intended to illustrate but not to limit the invention.

EXAMPLE 1

Effect of BPD-MA on CHS

The well documented delayed-type hypersensitivity (DTH) alternatively called the contact hypersensitivity (CHS) model was employed. Dinitrofluorobenzene (DNFB) was painted onto the inguinal area of hairless strain mice on day 0. On day 5, the DNFB is painted onto the ear, resulting in a measurable localized inflammatory response, including swelling of the ear, during the following 24 hours orchestrated by antigen-specific T cells.

Mice painted with DNFB on day 0 were injected intravenously with liposomal BPD-MA at a dose of 1 mg/kg on day −2, −1, 0, +1, +3 or +4. On day 5 the mice were challenged by painting DNFB onto the ear and ear swelling was measured 24 hours later. Minimal ear swelling was noted in unprimed mice. DNFB-sensitized mice administered saline rather than BPD-MA showed a strong ear-swelling response following challenge with DNFB. Swelling was recorded as percent swelling, or $$\frac{\text{ear thickness post-challenge minus ear thickness pre-challenge}}{\text{ear thickness pre-challenge}} \times 100$$

When BPD-MA was given on days −2, −1, 0, +1, or +3, ear swelling was less than 50% of that observed in the positive control animals. Inhibition of the CHS response was approximately 25% when BPD-MA was given on day 4.

In an additional experiment, mice that had been previously sensitized with DNFB were treated with a different skin contact sensitizer, oxazolone. The mice were subsequently challenged with DNFB and oxazolone. Mice treated with BPD-MA showed a diminished response to DNFB. However, no diminution in the ear swelling in response to oxazolone was found in mice administered BPD-MA. Thus, only the antigen-specific T cells (reactive to DNFB) were affected by BPD-MA. The mice retained their ability to respond to the second antigen, oxazolone, despite the treatment with BPD-MA in conjunction with DNFB sensitization.

EXAMPLE 2

Effect of BPD-MA on Skin Allograft Rejections

The skin allograft rejection assay involving skin grafts between MHC-incompatible mice was conducted according to the method of Medewar and Billingham in *The Technique of Free Skin Grafting in Mammals*, Journal of Experimental Biology, (1951), Vol. 28, pp.385–402,. Control mice (n=16) reject the grafts 11.1±1.9 days following allograft.

In the experimental group, (n=6) mice received a single intravenous injection of 0.25 mg/kg BPD-MA liposomal preparation 3–4 hours after allografting and showed prolonged engraftment to 20.7±0.9 days at rejection. Another group of mice who received an additional 0.25 mg/kg injection of BPD-MA on day 8 showed a mean rejection time of 23.3±1.9 days.

Thus, BPD-MA without deliberate, direct or transcutaneous irradiation appears to suppress rejection of allografts.

EXAMPLE 3

Experimental Testing of Various BPD Analogs on the CHS Response

A comparison of the influence of BPD-MA, BPD-MB, BPD-DA, and BPD-DB on the CHS response to the topically applied hapten DNFB, in the absence of direct or transcutaneously applied light was performed using the method outlined in Example 2 above. The compounds were evaluated in naive, unshaved Balb/c mice. Each treatment group consisted of 4–5 animals. BPD analogs were reconstituted in DMSO and administered 24 hours following DNFB application. Mice were ear challenged on day 5 of the experiment and the response measured one day later. The final DMSO concentration was 2%. Control mice received the appropriate, matched solvent.

Figures 1, 2:
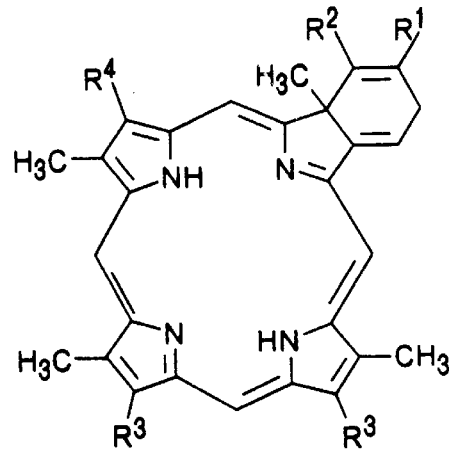
FIG. 2 shows a comparison of the influence of four BPD analogs on the DTH response in naive, unshaven Balb/c mice.
Figures 1, 2, 3:
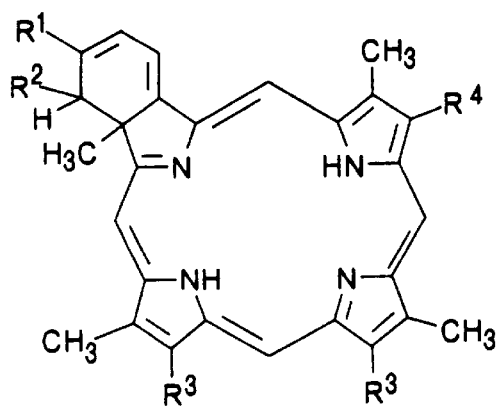

The results are provided in Tables 1 and 2 and summarized in FIG. 2. BPD-MA and BPD-MB strongly inhibited the CHS response. BPD-DA and BPD-DB inhibited the CHS response but to a lesser extent than either BPD-MA or BPD-MB.

TABLE 1

Effect of different BPD derivatives on the CHS response

| BPD derivative | ΔEarR (mm × 10 − 2) | SD |
|---|---|---|
| MA 0.1 mg/kg | 4.02 | 1.54 |
| MA 1.0 mg/kg | 1.8 | 1.28 |
| MB 0.1 mg/kg | 2.32 | 0.69 |
| MB 0.5 mg/kg | 2.4 | 0.49 |
| DA 0.1 mg/kg | 6.46 | 3.6 |
| DA 1.0 mg/kg | 4.16 | 1.44 |
| DB 0.1 mg/kg | 10.33 | 2.8 |
| DB 1.0 mg/kg | 5.48 | 2.79 |
| (+) Control | 6.53 | 1.87 |
| Irritant | 1.78 | 0.59 |
| Irrit-MB (1.0) | 1.5 | 0.23 |
| Irrit-DA (1.0) | 1.78 | 0.29 |
| Irrit-DB (1.0) | 0.85 | 0.47 |

TABLE 2

| Compound | Dose (mg/kg) | Relative Inhibition of the DTH Response |
|---|---|---|
| BPD-MA | 1.0 | +++ |
| BPD-MA | 0.1 | ++ |
| BPD-MB | 0.5 | +++ |
| BPD-MB | 0.1 | +++ |
| BPD-DA | 1.0 | ++ |
| BPD-DA | 0.1 | + |
| BPD-DB | 1.0 | + |
| BPD-DB | 0.1 | − |

EXAMPLE 4

Influence of Light Levels on Immunomodulation

The CHS assay set forth in Example 1 was repeated using various dosages of BPD-MA administered 24 hours following sensitization with DNFB and various light levels.

In one set of experiments, the results of which are shown in FIG. 3A–3C, it was again shown that ambient light was sufficient to sustain an immunomodulatory effect.

FIG. 3A shows that when 15 J/cm² of light was provided after the administration of various levels of BPD-MA, a minimum of approximately 0.1 mg/kg was required before significant inhibition of the CHS response occurred. Similar results were obtained as shown in FIG. 3C when ambient light was substituted for the fixed administration of 15 J/cm$^2$ of light. The deliberately administered light was supplied transcutaneously as described by Richter, A. et al. *Photochem Photobiol* (1994) 59:350–355. Briefly, the mice were placed in the dark for one hour after intravenous injection of BPD-MA and then placed in clear plexiglass containers. Light of a wavelength of 692±12 nm at 12.5 mW/cm$^2$ was delivered from light excitation diodes (LED) positioned above and below the subject. Thus, the total light dosage was determined by the time of deliberate irradiation from the LEDs. A comparison of FIGS. 3A and 3C shows that simple ambient light radiation gives the same results as administering 15 J/cm$^2$ of light.

FIG. 3B shows the results obtained when 1 mg/kg intravenous BPD-MA was administered at various light dosages. The results are the substantially the same over the entire spectrum.

The experiment was again conducted using intravenous administration of BPD-MA in a liposomal formulation at 1 mg/kg 24 hours after sensitization with DNFB. The mice were either maintained under ambient light or under light-protected conditions throughout the experimental period except for mice treated with transcutaneous light (15 J/cm$^2$) 1 hour postinjection.

Figures 1, 2, 3, 4:
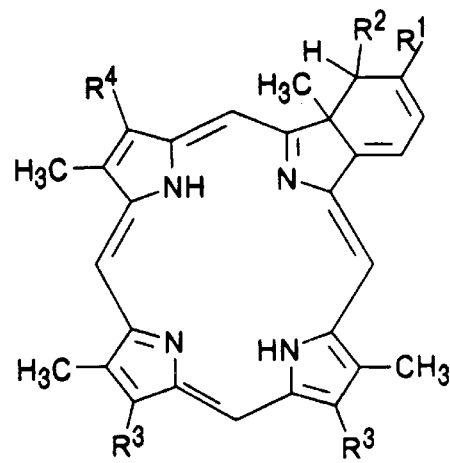
FIG. 4 shows a comparison of the CHS immune response of when mice are administered 1 mg/kg BPD-MA with various light protocols.

As shown in FIG. 4, mice which were sensitized with DNFB and received no treatment showed a change in ear thickness of approximately 15×10$^{-2}$ mm; light-protected mice receiving no BPD-MA showed similar changes. However, mice administered BPD-MA and not light-protected or treated with LED light showed a change of only approximately 11×10$^{-2}$ mm; mice treated with BPD-MA and protected from light showed an increase in thickness similar to controls—approximately 16–17×10$^{-2}$ mm. Mice administered BPD-MA and then treated with LED light showed increases of only about 7×10$^{-2}$ mm. Thus, at least ambient light is required in order to achieve the effect.

Figures 1, 2, 3, 4, 5:
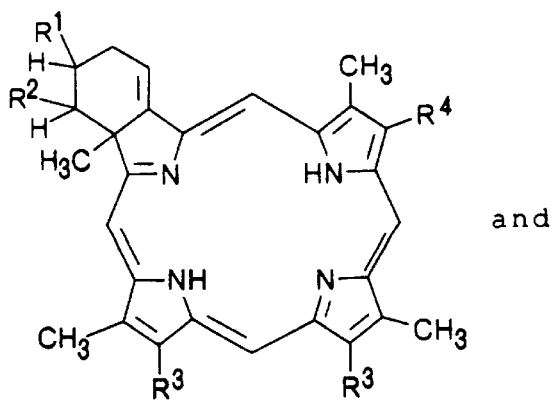
FIG. 5 shows the comparative effectiveness of BPD monoacids and BPD diacids in immunomodulation.

The various forms of BPD described above were compared for their effect on the CHS response; the compounds were administered at either 1 mg/kg 24 hours after DNFB sensitization or at 0.1 mg/kg using the same protocol (BPD-MB was administered at 0.5 mg/kg and 0.1 mg/kg). The mice were maintained under ambient light. As shown in FIG. 5, BPD-DB was the least effective of the four compounds tested; the monoacid forms were the most effective.

Figures 1, 2, 3, 4, 5, 6:
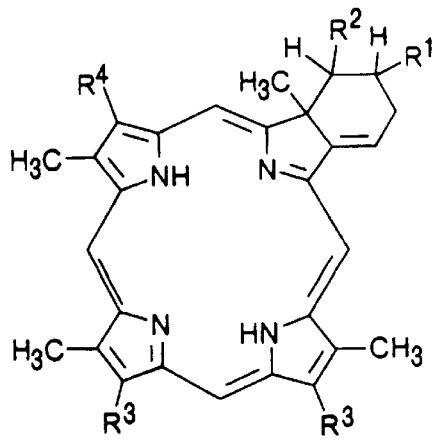
FIG. 6 shows the inability of non-green porphyrin photoactive compounds to modulate the immune response in the presence of ambient light.
Figure 2:
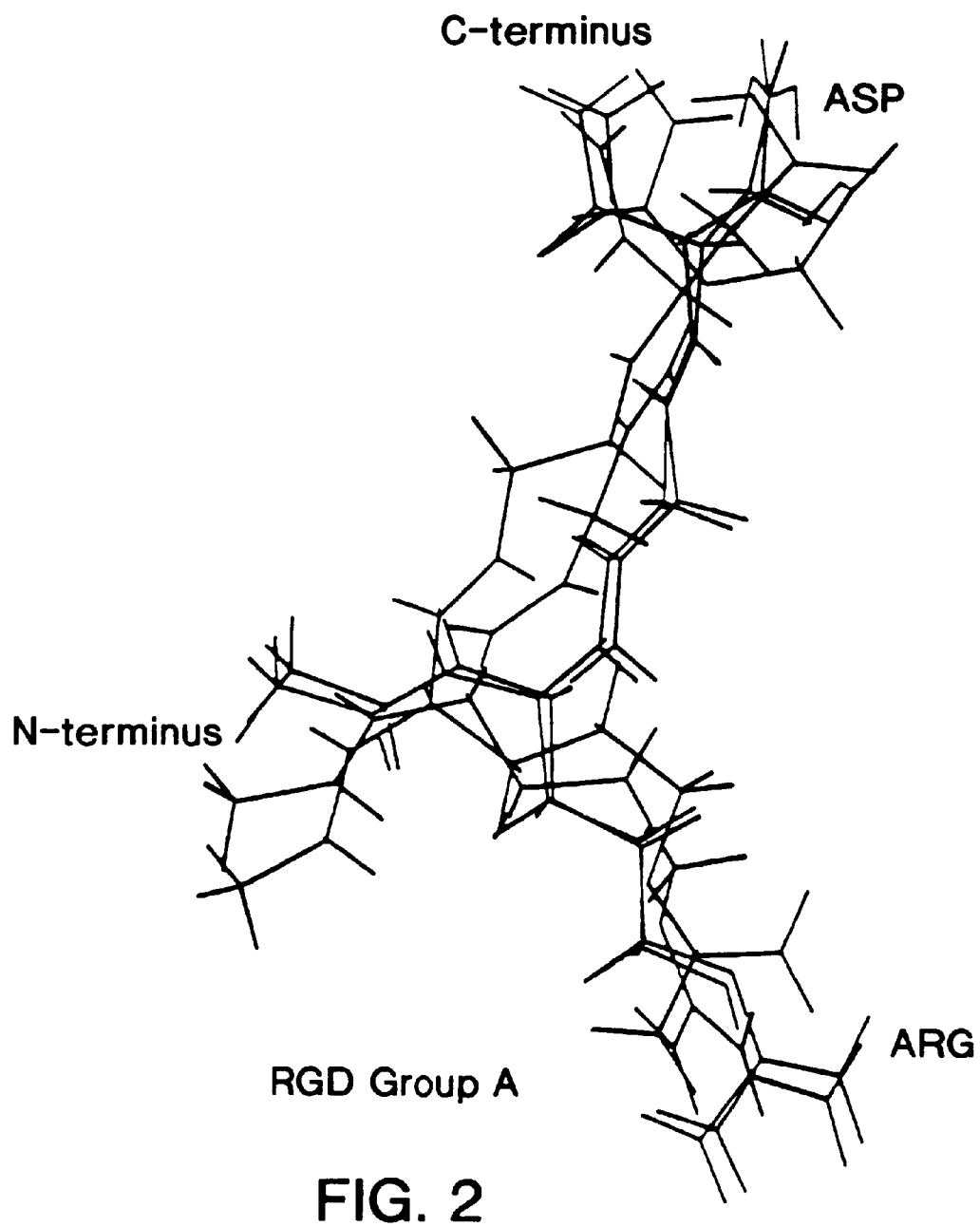
Figure 3:
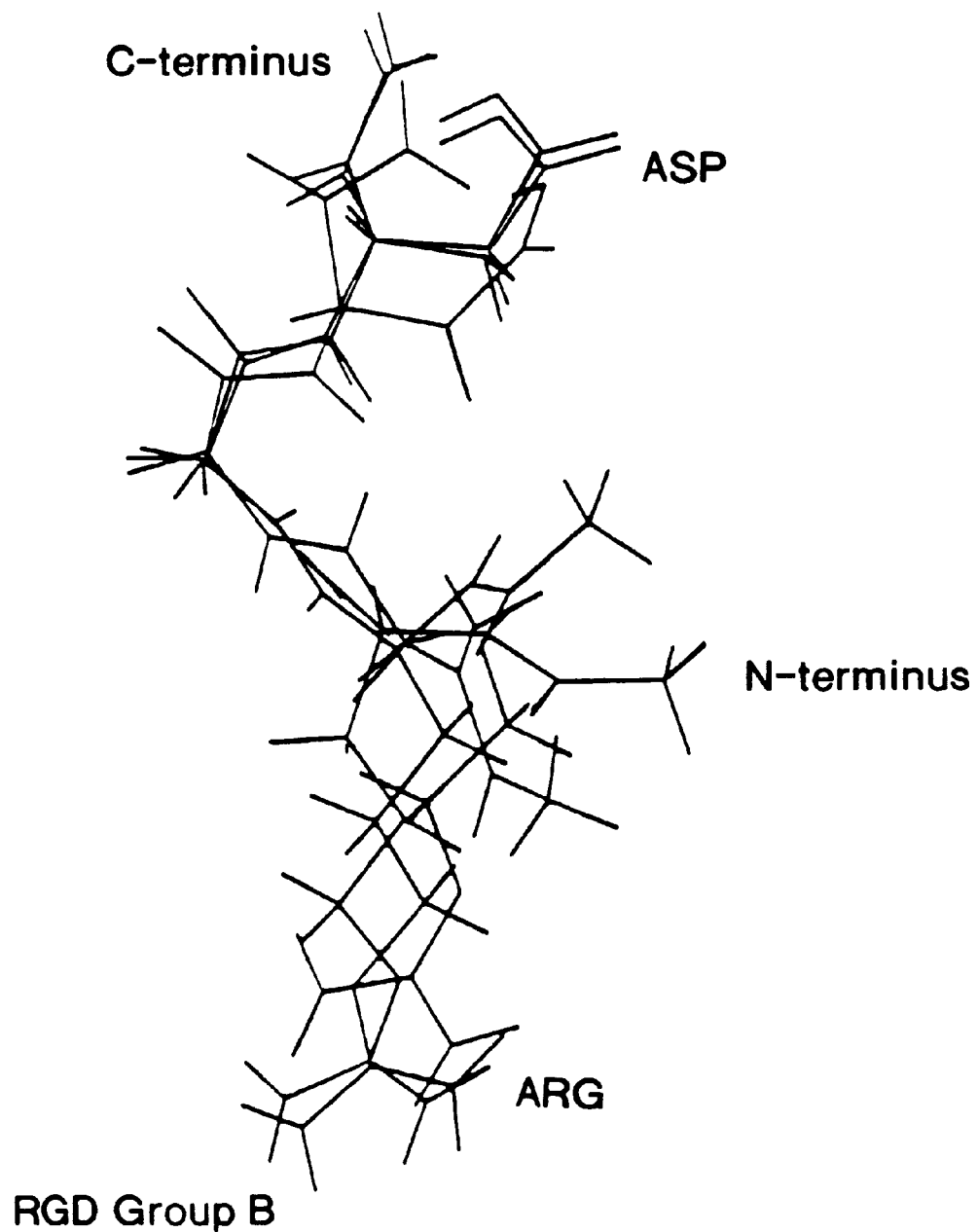
FIGS. 3A, 3B and 3C show the effects of various concentrations of BPD-MA and various light levels on immune response in a CHS model.
Figure 4:
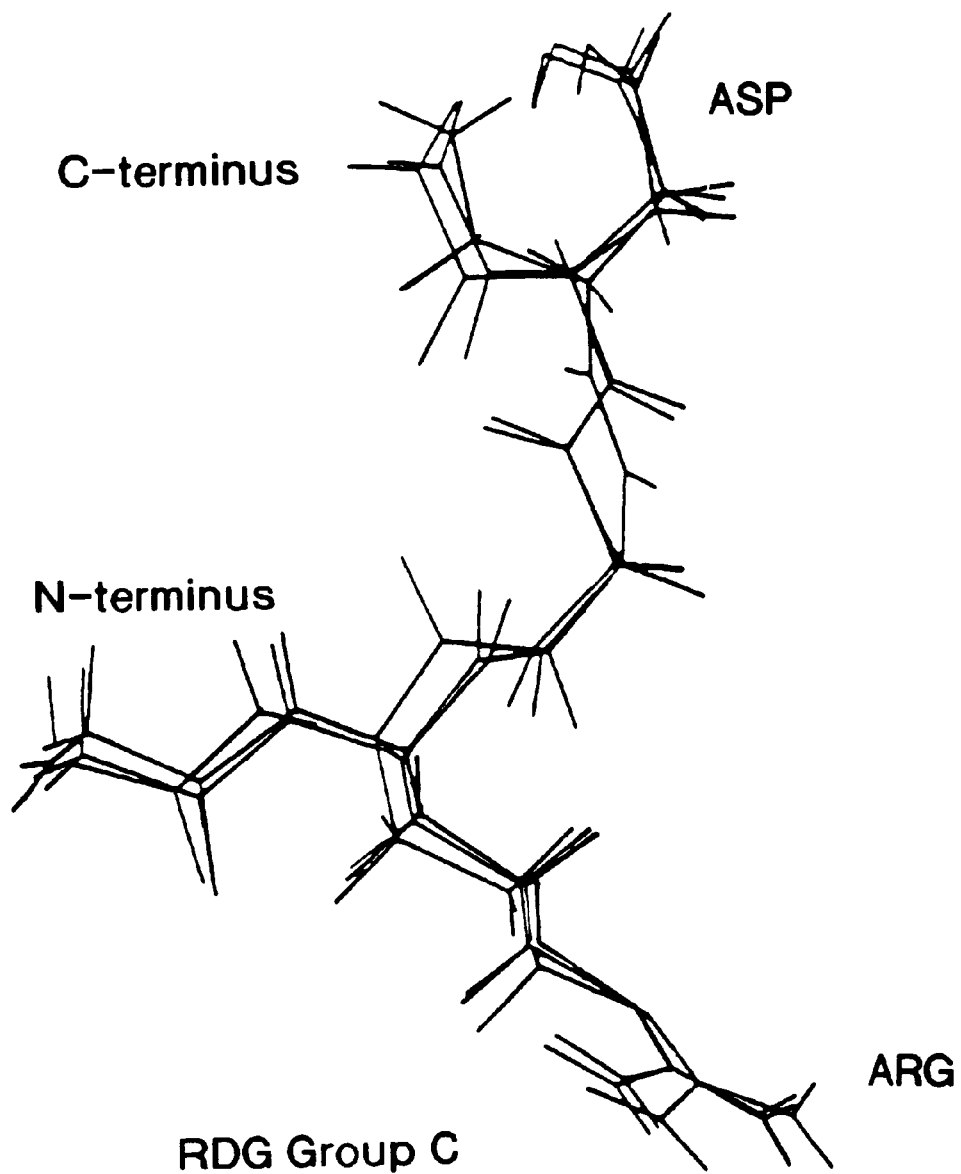
Figure 5:
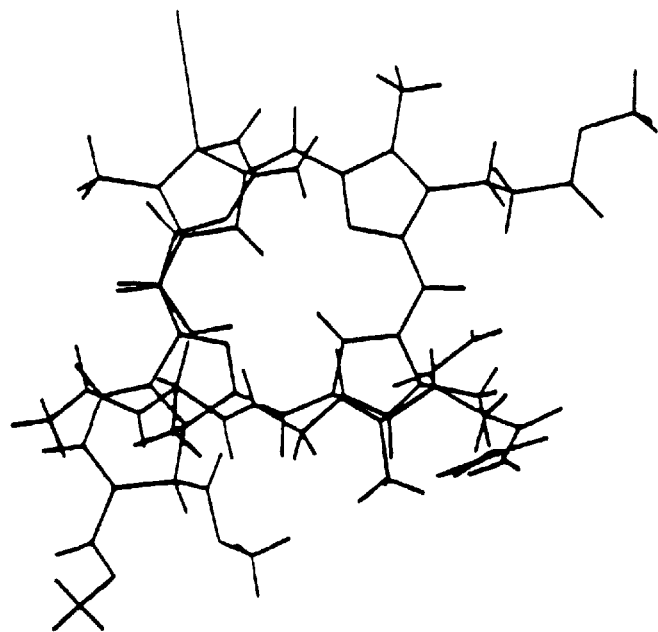
Figure 6:
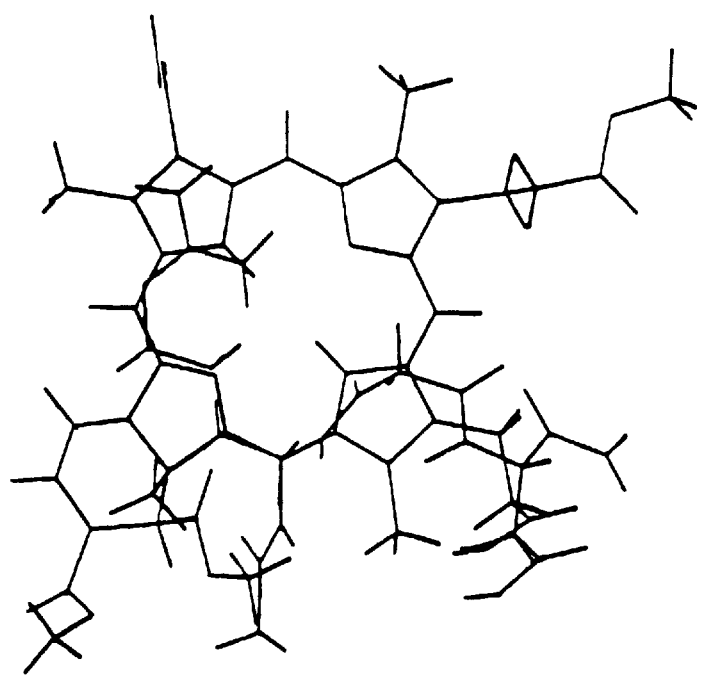
Figure 7:
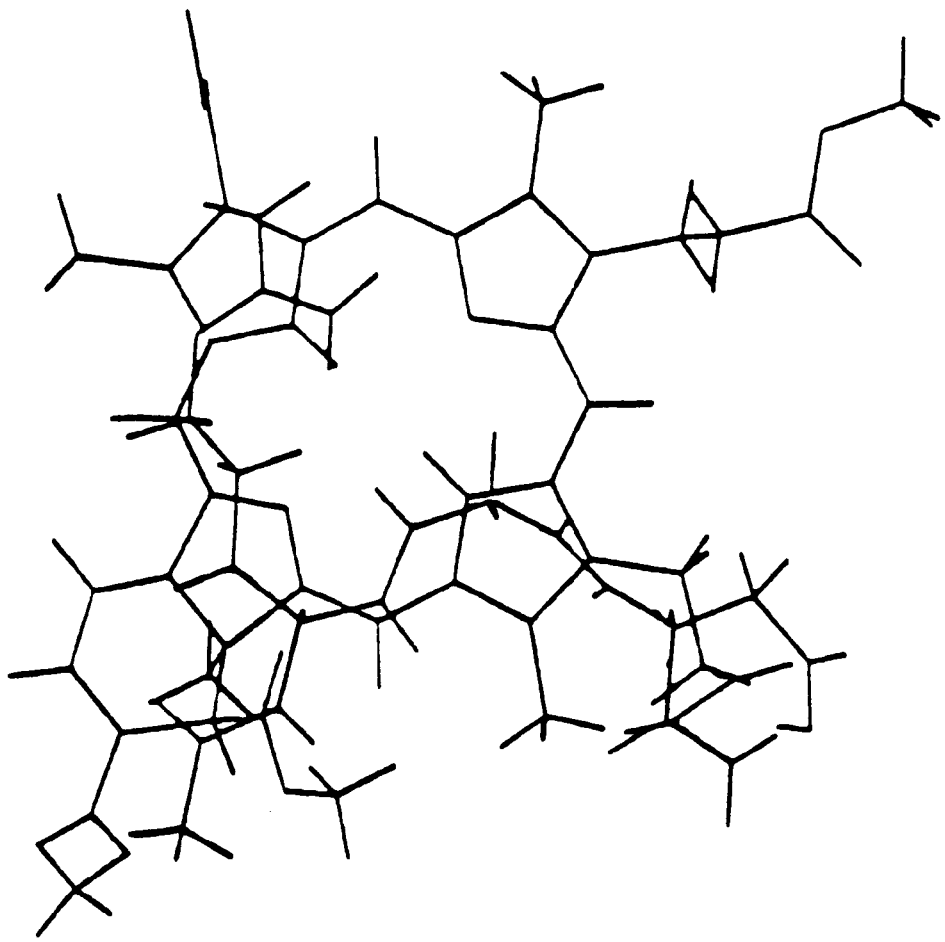

Other photosensitizers were also tested including Photofrin® porfirner sodium, zinc phthalocyanine and tin etioporphyrin. The results, shown in FIG. 6, indicate that these alternative photoactive compounds commonly used in PDT were not significantly effective in modulating the immune response under ambient radiation. Tin etioporphyrin at 1 mg/kg was completely ineffective. Photofrin® porfirner sodium at 2.5 mg/kg and zinc phthalocyanine at 1 mg/kg or 0.14 mg/kg did not significantly affect the ear swelling response.

EXAMPLE 5

Drug Dosage/Light Level Parameters in Effecting Immune Response

The contact hypersensitivity assay (CHS assay) described in Example 2 was employed. Groups of DBA/2 mice (4–8 per group) were treated one day prior to sensitization using various photodynamic therapy (PDT) regimes as described below. Twenty-four hours following PDT, mice were sensitized by epicutaneous application of 35 µl of 0.5% DNFB solution in acetone:olive oil (4:1) on the left flank. Contact hypersensitivity was elicited by applying 10 µl of a 0.25% DNFB solution on the inner portion of the left ear 5 days after sensitization. Ear thickness was measured using a dial thickness gauge before application of the challenge dose of DNFB and 24 hours thereafter. The difference between the two readings was recorded as ear swelling. Percent suppression was calculated as follows:

$$\frac{\text{Ear swelling of control group} - \text{ear swelling of treated group}}{\text{Ear swelling of control group}} \times 100 = \% \text{ supression}$$

In an initial experiment, mice received either no treatment (controls); 1 mg/kg BPD-MA without light; UVA light alone without BPD-MA; or a combination of 1 mg/kg BPD-MA plus UVA light. In the protocols, BPD-MA was administered in liposomal form to the animals intravenously via tail vein. The animals were placed in the dark for 1 hour; animals receiving light were then exposed at 10 mW/cm$^2$ for 8 min. and 20 sec. to provide a total of 5.0 J/cm$^2$ of light in the wavelength range 320–420 nm.

The control group showed an ear swelling of 0.083 mm on the average; the percent suppression in animals treated with light alone, BPD-MA alone, or a combination is shown in Table 3.

TABLE 3

| Light | BPD-MA | % Suppression |
| --- | --- | --- |
| 0 | 1 mg/kg | 20 |
| 5.0 J/cm$^2$ UVA* | 0 | 27 |
| 5.0 J/cm$^2$ UVA* | 1 mg/kg | 57 |

*Light intensity 10 mW/cm$^2$ for 8 min. and 20 sec.

As shown, the combination is more effective than either BPD-MA or UVA alone in inhibiting the immune response as measured by CHS.

In a second experiment, the same protocol was followed except that broad spectrum light (BSL) in a wavelength range of 300–900 nm was applied at 11.85 mW/cm$^2$ for 7 min. to provide a total energy of 5 J/cm$^2$. The control group in this experiment showed a mean ear swelling of 0.074 mm. The results in terms of percent suppression are shown in Table 4.

TABLE 4

| Light | BPD-MA | % Suppression |
| --- | --- | --- |
| 0 | 1 mg/kg | 22 |
| 5.0 J/cm$^2$ BSL* | 0 | 24 |
| 5.0 J/cm$^2$ BSL* | 1 mg/kg | 45 |

*Light intensity 11.85 mW/cm$^2$ or 7 min.

Again, the combination of drug and low-level broad-spectrum light was more effective in suppression of swelling than either light or drug alone.

In a third experiment, mice were subjected to the foregoing protocol except that the BPD-MA was administered at either 1 mg/kg or 2 mg/kg and the broad-spectrum light was administered at a lower intensity—300 µW/cm$^2$ (200–400 µW/cm$^2$) for a mean time of 5 hours. Thus, the total energy of 5.0 J/cm$^2$ was maintained. The control group showed a mean ear swelling of 0.089 mm. In this experiment, BPD-MA at 1 mg/kg alone showed a mean swelling in the group somewhat higher than the controls so the percent suppression was not determinable.

The results are shown in Table 5.

TABLE 5

| Light | BPD-MA | % Suppression |
|---|---|---|
| 0 | 1 mg/kg | slightly higher |
| 0 | 2 mg/kg | 18 |
| 5.0 J/cm² BSL* | 1 mg/kg | 20 |
| 5.0 J/cm² BSL* | 2 mg/kg | 40 |

*Light intensity 300 μW/cm² for 5 hours.

As shown, at this lower intensity, the combination of 2 mg/kg with 5 J/cm² BSL provided a percent suppression comparable to the previous results.

In a fourth experiment, the broad spectrum light was supplied at 110 μW/cm² for 6 hours to provide a total energy of 2.4 J/cm². The ear swelling in the control group was 0.115 mm. Table 6 shows the percent suppression under various treatment conditions. Again, significant suppression occurred only with the combination of a 2 mg/kg dose of BPD-MA administered with the light treatment.

TABLE 6

| Light | BPD-MA | % Suppression |
|---|---|---|
| 0 | 1 mg/kg | 12 |
| 0 | 2 mg/kg | 16 |
| 2.4 J/cm² BSL* | 1 mg/kg | 23 |
| 2.4 J/cm² BSL* | 2 mg/kg | 43 |

*Light intensity 110 μW/cm² for 6 hours.

EXAMPLE 6

Effect of Low Intensity PDT on Cell Culture

Various cell cultures representing a variety of cell types were tested as substrates for PDT under varying doses of BPD-MA and irradiation. In a typical experiment, 100 μl of the cell culture were treated in 96-well flat-bottomed tissue culture plates in replicates of six. BPD-MA was added and the plates then incubated in the dark at 37° C. for 1 hour. Light exposure was conducted at room temperature. After exposure to light, tissue culture medium was added to the cells to provide a final volume of 200 μl/well and the plates were incubated in a humidified $CO_2$ incubator at 37° C. for 18–20 hours. Cell viability was assessed using an MTT assay (Mosmann, T., *J Immunol Meth* (1983) 65:55–63). The percent viability was calculated as the difference between the viability of the control group and the treatment group divided by the viability of the control group×100.

In the first experiment, an adherent keratinocyte cell line, PAM212 was treated with BPD-MA in the range of 1.25–320 ng/mL at various light levels: 1 J/cm² UVA light (320–420 nm) at 5 mW/cm² for 3 min., 25 sec.; and in the range of 0.4–1.2 J/cm² broad spectrum light (300–900 nm) at 117 mW/cm² for 1, 2 or 3 hours to provide 0.4, 0.8 or 1.2 J/cm². The results are shown in Table 7.

TABLE 7

| | BPD-MA Concentration (ng/mL) | | | | | | | | | |
|---|---|---|---|---|---|---|---|---|---|---|
| Plate | 0 | 1.25 | 2.5 | 5 | 10 | 20 | 40 | 80 | 160 | 320 |
| 1 | 100 | 111 | 107 | 106 | 105 | 108 | 110 | 124 | 122 | 124 |
| 2 | 85 | 90 | 100 | 97 | 100 | 82 | 77 | 6 | 12 | 10 |
| 3 | 89 | 91 | 82 | 88 | 71 | 82 | 87 | 70 | 55 | 24 |
| 4 | 90 | 94 | 90 | 86 | 88 | 87 | 68 | 53 | 23 | 8 |
| 5 | 84 | 97 | 94 | 90 | 86 | 75 | 58 | 54 | 11 | 7 |

Plate 1: BPD-MA alone.
Plate 2: BPD-MA plus 1.0 J/cm² UVA. 5 mW/cm² for 3 min. 26 sec.
Plate 3: BPD-MA plus 0.4 J/cm² broad spectrum light. 117 μW/cm² for 1 hour.
Plate 4: BPD-MA plus 0.8 J/cm² broad spectrum light. 117 μW/cm² for 2 hours.
Plate 3: BPD-MA plus 1.2 J/cm² broad spectrum light. 117 μW/cm² for 3 hours.

Significant decreases in viability were obtained at all light dosages at concentrations of 320 ng/mL and at 160 ng/mL. $LD_{50}$ values for BPD-MA and 0.4, 0.8 and 1.2 J/cm² BSM were 200, 96 and 93 ng/mL respectively, whereas the $LD_{50}$ value using 1.0 J/cm² UVA light was 110 ng/mL.

In a second experiment, mouse splenocytes activated by Concanavalin A for 48 hours were treated in a concentration of BPD-MA of 1.25–160 ng/mL with or without 0.5–1.5 J/cm² broad spectrum light supplied at 255 μW/cm² for 32, 65 or 98 min. to provide 0.5, 1.0 or 1.5 J/cm² total energy; 1 J/cm² UVA light supplied at 5 mW/cm² for 3 min. 25 sec. or with 1 J/cm² LED light supplied at 34(?) mW for 30 sec. The results of experiment are shown in Table 8.

TABLE 8

| | BPD-MA Concentration (ng/mL) | | | | | | | | |
|---|---|---|---|---|---|---|---|---|---|
| Plate | 0 | 1.25 | 2.5 | 5 | 10 | 20 | 40 | 80 | 160 |
| 1 | 100 | 94 | 96 | 94 | 100 | 96 | 94 | 102 | 101 |
| 2 | 102 | 98 | 102 | 96 | 96 | 88 | 76 | 36 | 26 |
| 3 | 100 | 100 | 91 | 91 | 87 | 67 | 33 | 24 | 22 |
| 4 | 97 | 96 | 94 | 93 | 74 | 41 | 28 | 23 | 26 |
| 5 | 101 | 100 | 90 | 95 | 90 | 63 | 36 | 28 | 29 |
| 6 | 91 | 87 | 85 | 80 | 76 | 49 | 31 | 25 | 25 |

Plate 1: BPD-MA alone.
Plate 2: BPD-MA plus 0.5 J/cm² broad spectrum light. 255 μW/cm² for 32 min.
Plate 3: BPD-MA plus 1 J/cm² broad spectrum light. 255 μW/cm² for 65 min.
Plate 4: BPD-MA plus 1.5 J/cm² broad spectrum light. 255 μW/cm² for 98 min.
Plate 5: BPD-MA plus 1.0 J/cm² LED light. 34 mW/cm² for 30 sec.
Plate 6: BPD-MA plus 1.0 J/cm² UVA light. 5 mW/cm² for 3 min. 25 sec.

As shown in Table 9, BPD-MA activated by broad spectrum light kills cells in a drug and light-dose-dependent manner. The BPD-MA $LD_{50}$ values for cells at 0.5, 1.0 and 1.5 J/cm² respectively were 50, 22 and 13 ng/mL. The $LD_{50}$ values for BPD-MA and 1.0 J/cm² of BSL, LED or UVA light were 22, 20 and 14 ng/mL respectively.

These results show that splenocytes appear more susceptible to PDT than the keratinocyte population.

In additional experiments, the monocyte origin cell line U937, and the T cell lines CEM and H9 were subjected to the protocols of the previous experiment except that the BSL was supplied at 182 μW/cm² for mean exposure times of 47, 93 and 140 min. respectively to provide 0.5, 1.0 and 1.5 J/cm² respectively. The results of these experiments are shown in Table 9.

TABLE 9

Mean cell viability (percent) ± s.d.

| BPD-MA (ng/mL) | 0.5 J/cm² BSL | 1.0 J/cm² BSL | 1.5 J/cm² BSL | 1.0 J/cm² LED | 1.0 J/cm² UVA |
|---|---|---|---|---|---|
| U937 | | | | | |
| 0 | 100 | 100 | 100 | 100 | 100 |
| 2.5 | 93 ± 4 | 92 ± 4 | 94 ± 5 | 97 ± 2 | 92 ± 4 |
| 5 | 93 ± 4 | 81 ± 1 | 87 ± 10 | 87 ± 3 | 88 ± 4 |
| 10 | 86 ± 3 | 74 ± 4 | 54 ± 12 | 82 ± 9 | 81 ± 5 |
| 20 | 67 ± 6 | 87 ± 9 | 24 ± 10 | 65 ± 17 | 63 ± 11 |
| 40 | 25 ± 6 | 13 ± 5 | 13 ± 5 | 36 ± 15 | 27 ± 15 |
| 80 | 11 ± 3 | 10 ± 7 | 11 ± 6 | 15 ± 7 | 14 ± 8 |
| 160 | 10 ± 0 | 5 ± 3 | 7 ± 6 | 12 ± 1 | 6 ± 4 |
| CEM | | | | | |
| 0 | 100 | 100 | 100 | 100 | 100 |
| 2.5 | 94 ± 2 | 90 ± 7 | 92 ± 1 | 95 ± 3 | 85 ± 4 |
| 5 | 85 ± 2 | 82 ± 12 | 75 ± 4 | 95 ± 7 | 82 ± 4 |
| 10 | 84 ± 8 | 64 ± 16 | 55 ± 14 | 86 ± 3 | 73 ± 8 |
| 20 | 59 ± 13 | 29 ± 12 | 24 ± 6 | 60 ± 13 | 41 ± 12 |
| 40 | 24 ± 7 | 14 ± 8 | 14 ± 7 | 21 ± 9 | 18 ± 10 |
| 80 | 14 ± 5 | 14 ± 10 | 15 ± 9 | 15 ± 6 | 16 ± 10 |
| 160 | 8 ± 6 | 8 ± 4 | 10 ± 5 | 10 ± 4 | 10 ± 4 |
| H9 | | | | | |
| 0 | 100 | 100 | 100 | 100 | 100 |
| 2.5 | 89 ± 4 | 96 ± 3 | 87 ± 3 | 92 ± 3 | 82 ± 5 |
| 5 | 89 ± 5 | 92 ± 5 | 78 ± 5 | 88 ± 7 | 89 ± 3 |
| 10 | 90 ± 6 | 88 ± 4 | 67 ± 4 | 88 ± 4 | 83 ± 9 |
| 20 | 77 ± 12 | 61 ± 10 | 39 ± 8 | 73 ± 9 | 68 ± 13 |
| 40 | 48 ± 5 | 46 ± 11 | 26 ± 3 | 53 ± 10 | 40 ± 10 |
| 80 | 24 ± 3 | 27 ± 5 | 22 ± 3 | 23 ± 6 | 23 ± 7 |
| 160 | 19 ± 6 | 19 ± 5 | 12 ± 2 | 14 ± 1 | 15 ± 1 |

As shown, viability was impaired at BPD-MA concentrations of approximately 20 ng/mL all light intensities supplied.

The $LD_{50}$ values for these cell lines at various light concentrations are shown, in units of ng/mL in Table 10.

TABLE 10

BPD-MA $LD_{50}$ Values (ng/mL)

| | 0.5 J/cm² BSL | 1.0 J/cm² BSL | 1.5 J/cm² BSL | 1.0 J/cm² LED | 1.0 J/cm² UVA |
|---|---|---|---|---|---|
| U937 | 27 | 17 | 12 | 28 | 26 |
| CEM | 24 | 15 | 12 | 24 | 18 |
| H9 | 38 | 27 | 15 | 45 | 32 |

The $LD_{50}$ values appear dependent on the total level of light.

In an additional experiment, the effect of intensity of the light delivered was tested with U937 cells in the protocols described above. BPD-MA was supplied at 2.5–80 ng/mL and 1.0 J/cm² LED light was delivered at intensities of 250 μW/cm² to 50 mW/cm². Thus, the LED light was delivered at 50, 10, 1 and 0.250 mW cm² for 20, 100, 1000 and 4000 sec. respectively. The results are shown in Table 11.

TABLE 11

Mean cell viability (percent) ± s.d.

| BPD-MA (ng/mL) | No light | 50 mW/cm² | 10 mW/cm² | 1 mW/cm² | 250 μW/cm² |
|---|---|---|---|---|---|
| 0 | 100 | 98 | 91 | 92 | 92 |
| 2.5 | 104 | 94 | 91 | 89 | 92 |
| 5 | 98 | 84 | 87 | 82 | 79 |
| 10 | 92 | 82 | 81 | 79 | 73 |
| 20 | 94 | 66 | 72 | 65 | 68 |
| 40 | 94 | 81 | 45 | 40 | 44 |
| 80 | 90 | 8 | 17 | 14 | 18 |

As shown in Table 11, the viability appeared relatively independent of light intensity, especially at low doses of BPD-MA.

We claim:

1. A method to modulate an antigen-specific immune response which method comprises administering to a subject in need of such modulation, an amount of green porphyrin effective to modulate said immune response to the antigen, said administering being performed during the ongoing antigen-specific immune response to said antigen, and maintaining said subject in ambient light for a sufficient time to effect immunomodulation, but maintaining viability of the cells of said subject.

2. The method of claim 1 wherein said green porphyrin is administered systemically in a liposomal composition.

3. The method of claim 1 wherein said antigen is an autoantigen.

4. The method of claim 1 wherein said subject is the recipient of foreign tissue.

5. The method of claim 1 wherein said antigen is associated with psoriasis.

6. The method of claim 1 wherein said antigen is an allergen.

7. The method of claim 1 wherein said green porphyrin is of the formula,

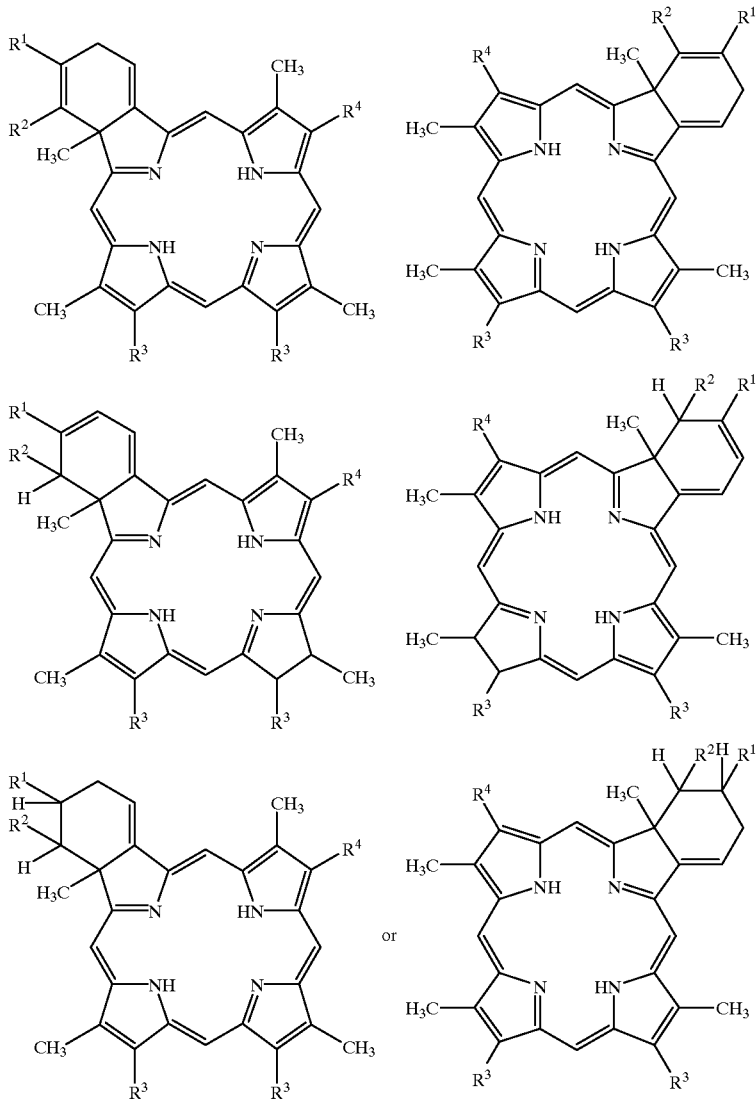

or a mixture thereof, wherein each of $R^1$ and $R^2$ is independently selected from the group consisting of carbalkoxyl (2–6C); alkyl (1–6C); arylsufonyl (6–10C); cyano; and —CONR$^5$CO— wherein $R^5$ is aryl (6–10C) or alkyl (1–6C);

each $R^3$ is independently carboxyl, carboxyalkyl (2–6C) or a salt, amide, ester or acylhydrazone or is alkyl (1–6C); p1 $R^4$ is CH=CH$_2$ or —CH(OR$^{4'}$)CH$_3$ wherein $R^{4'}$ is H, or alkyl (1–6C) optionally substituted with a heteroatom substituent.

8. The method of claim 7 wherein said green porphyrin is of the formula,

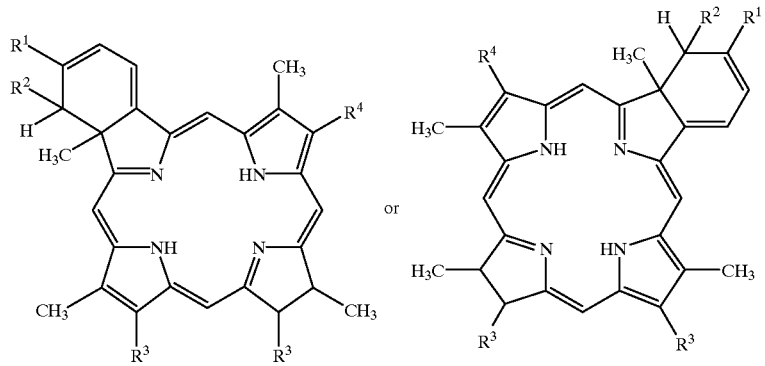

or a mixture thereof, and wherein each of $R^1$ and $R^2$ is independently carbalkoxyl (2–6C);
one $R^3$ is carboxyalkyl (2–6C) and the other $R^3$ is the ester of a carboxyalkyl (2–6C) substituent; and
$R^4$ is CH=CH$_2$ or —CH(OH)CH$_3$.

9. The method of claim 8 wherein said green porphyrin is of the formula

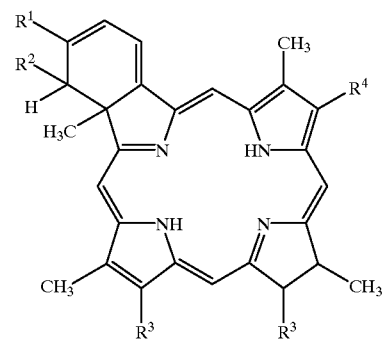

and wherein $R^1$ and $R^2$ are methoxycarbonyl;
one $R^3$ is —CH$_2$CH$_2$COOCH$_3$ and the other $R^3$ is CH$_2$CH$_2$COOH; and
$R^4$ is CH=CH$_2$.

10. The method of claim 7 wherein said green porphyrin is of the formula

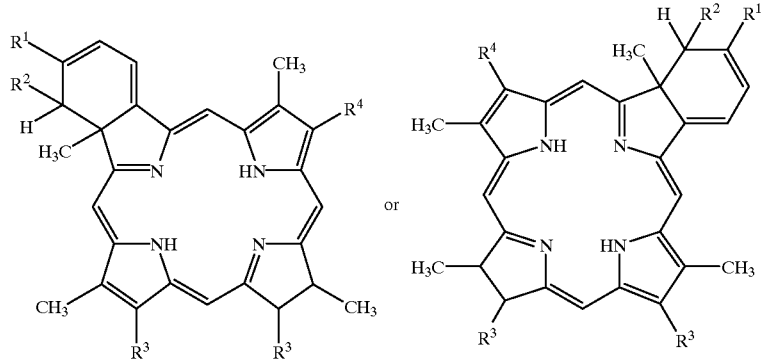

and wherein $R^1$ is —COOH, $R^2$ is methoxycarbonyl, both $R^3$ are —CH$_2$CH$_2$COOH, and $R^4$ is —CH=CH$_2$.

11. The method of claim 7 wherein said green porphyrin is of the formula

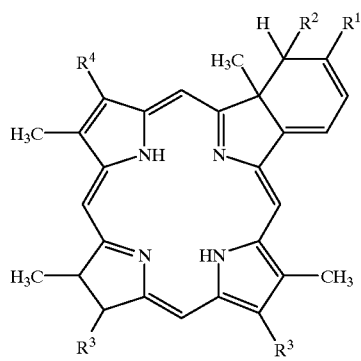

and wherein $R^1$ and $R^2$ are methoxycarbonyl, both $R^3$ are —CH$_2$CH$_2$COOCH$_2$CH$_2$OH, and $R^4$ is —CH=CH$_2$.

12. The method of claim 1 wherein said ambient light is less than one-quarter the total energy of light required to induce erythema in said subject after administering said effective amount of green porphyrin.

13. The method of claim 1 wherein said ambient light is less than 10 J/cm$^2$.

14. The method of claim 1 wherein said ambient light is applied at an intensity of less than 500 $\mu$W/cm$^2$.

15. The method of claim 9 wherein said effective amount is 1–2 mg/kg.

* * * * *

UNITED STATES PATENT AND TRADEMARK OFFICE

CERTIFICATE OF CORRECTION

PATENT NO. : 6,008,241

DATED : December 28, 1999

INVENTOR(S) : Agnes H. Chan et al.

It is certified that error appears in the above-identified patent and that said Letters Patent is hereby corrected as shown below:

On the title page, item: line [73] Assignee:, should read --QLT PhotoTherapeutics, Inc., Vancouver, Canada; and The University of British Columbia, Vancouver, Canada.--

Signed and Sealed this

Thirty-first Day of October, 2000

Attest:

Q. TODD DICKINSON

*Attesting Officer*      *Director of Patents and Trademarks*